US010209501B2

(12) United States Patent
Hou et al.

(10) Patent No.: US 10,209,501 B2
(45) Date of Patent: Feb. 19, 2019

(54) 3D MICROSCOPE AND METHODS OF MEASURING PATTERNED SUBSTRATES

(71) Applicant: Zeta Instruments, Inc., San Jose, CA (US)

(72) Inventors: Zhen Hou, Fremont, CA (US); James Jianguo Xu, San Jose, CA (US); Ken Kinsun Lee, Los Altos Hills, CA (US); James Nelson Stainton, San Jose, CA (US); Hung Phi Nguyen, Santa Clara, CA (US); Rusmin Kudinar, Fremont, CA (US); Ronny Soetarman, Fremont, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 160 days.

(21) Appl. No.: 15/150,406

(22) Filed: May 9, 2016

(65) Prior Publication Data

US 2016/0253813 A1     Sep. 1, 2016

Related U.S. Application Data

(63) Continuation of application No. 13/172,686, filed on Jun. 29, 2011, now Pat. No. 9,389,408.

(Continued)

(51) Int. Cl.
*G06T 7/00* (2017.01)
*G02B 21/00* (2006.01)
(Continued)

(52) U.S. Cl.
CPC ....... *G02B 21/006* (2013.01); *G01N 21/9501* (2013.01); *G01N 21/956* (2013.01);
(Continued)

(58) Field of Classification Search
CPC ........................... G02B 21/06; H04N 13/0207
(Continued)

(56) References Cited

U.S. PATENT DOCUMENTS 2,977,847 A  4/1961 Meyer-Arendt
3,437,395 A  4/1969 Rosenberger et al.
(Continued)

FOREIGN PATENT DOCUMENTS

CN   101034198 A   9/2007

OTHER PUBLICATIONS

Cole et al. "Time-domain whole-field fluorescence lifetime imaging with optical sectioning", Journal of Microscopy, vol. 203, Pt. 3, Sep. 2001, pp. 246-257.

*Primary Examiner* — Richard T Torrente
(74) *Attorney, Agent, or Firm* — Bever, Hoffman & Harms, LLP

(57) ABSTRACT

A three-dimensional (3D) microscope for patterned substrate measurement can include an objective lens, a reflected illuminator, a transmitted illuminator, a focusing adjustment device, an optical sensor, and a processor. The focusing adjustment device can automatically adjust the objective lens focus at a plurality of Z steps. The optical sensor can be capable of acquiring images at each of these Z steps. The processor can control the reflected illuminator, the transmitted illuminator, the focusing adjustment device, and the optical sensor. The processor can be configured to capture first and second images at multiple Z steps, the first image with the pattern using the reflected illuminator and the second image without the pattern using one of the reflected illuminator and the transmitted illuminator.

15 Claims, 13 Drawing Sheets

Related U.S. Application Data

(60) Provisional application No. 61/367,352, filed on Jul. 23, 2010.

(51) Int. Cl.
  *G01N 21/956* (2006.01)
  *G02B 21/36* (2006.01)
  *G01N 21/95* (2006.01)
  *G06T 7/60* (2017.01)
  *G01N 21/01* (2006.01)

(52) U.S. Cl.
  CPC ..... *G02B 21/0016* (2013.01); *G02B 21/0028* (2013.01); *G02B 21/0032* (2013.01); *G02B 21/367* (2013.01); *G06T 7/60* (2013.01); *G01N 2021/0168* (2013.01); *G06T 2207/10056* (2013.01); *G06T 2207/10152* (2013.01); *G06T 2207/20068* (2013.01); *G06T 2207/30148* (2013.01)

(58) Field of Classification Search
  USPC ...................................... 348/46, 50
  See application file for complete search history.

(56) References Cited

U.S. PATENT DOCUMENTS

| | | |
|---|---|---|
| 4,198,571 A | 4/1980 | Shappard |
| 4,629,324 A | 12/1986 | Stern |
| 4,692,051 A | 9/1987 | Stansbury, Jr. et al. |
| 4,852,985 A | 8/1989 | Fujihara et al. |
| 4,995,716 A | 2/1991 | Wamicki et al. |
| 5,022,743 A | 6/1991 | Kino |
| 5,151,609 A | 9/1992 | Nakagawa |
| 5,184,021 A | 2/1993 | Smith |
| 5,381,236 A | 1/1995 | Morgan |
| 5,528,033 A | 6/1996 | Lo et al. |
| 5,867,610 A | 2/1999 | Lee |
| 5,932,872 A | 8/1999 | Price |
| 6,088,155 A | 7/2000 | Tandler et al. |
| 6,275,335 B1 | 8/2001 | Costales |
| 6,323,953 B1 | 11/2001 | Blaesing-Bangert et al. |
| 6,376,818 B1 | 4/2002 | Wilson et al. |
| 6,539,331 B1 | 3/2003 | Fiekowsky |
| 6,616,291 B1 | 9/2003 | Love |
| 6,657,236 B1 | 12/2003 | Thibeault et al. |
| 7,384,809 B2 | 6/2008 | Donofrio |
| 7,683,386 B2 | 3/2010 | Tanaka et al. |
| 7,704,763 B2 | 4/2010 | Fujii et al. |
| 7,729,049 B2 | 6/2010 | Xu et al. |
| 7,745,245 B2 | 6/2010 | Niki et al. |
| 7,944,609 B2 | 5/2011 | Xu et al. |
| 8,174,762 B2 | 5/2012 | Xu et al. |
| 2003/0060809 A1 | 3/2003 | Wang et al. |
| 2004/0210402 A1 | 10/2004 | Opsal et al. |
| 2004/0257360 A1 | 12/2004 | Sieckmann |
| 2005/0046702 A1 | 3/2005 | Katayama et al. |
| 2006/0007533 A1 | 1/2006 | Eichhorn et al. |
| 2006/0038144 A1 | 2/2006 | Maddison |
| 2007/0109633 A1 | 5/2007 | Stelzer |
| 2007/0171519 A1 | 7/2007 | Wolleschensky |
| 2007/0212049 A1 | 9/2007 | Guroglu et al. |
| 2008/0067916 A1 | 3/2008 | Hsu et al. |
| 2008/0291532 A1* | 11/2008 | Xu .......... G02B 21/06 359/383 |
| 2008/0291533 A1 | 11/2008 | Xu et al. |
| 2009/0078888 A1 | 3/2009 | Namba et al. |
| 2009/0237676 A1 | 9/2009 | Kiers et al. |
| 2010/0074489 A1 | 3/2010 | Bacus et al. |
| 2010/0134595 A1* | 6/2010 | Xu .......... G02B 21/06 348/46 |
| 2010/0135573 A1 | 6/2010 | Xu et al. |
| 2011/0110567 A1 | 5/2011 | Jiang |

\* cited by examiner

3D MICROSCOPE AND METHODS OF MEASURING PATTERNED SUBSTRATES

RELATED APPLICATIONS

This application is a continuation of U.S. patent application Ser. No. 13/172,686, entitled "#D Microscope And Methods Of Measuring Patterned Substrates", filed Jun. 29, 2011 which claims priority to Provisional Application 61/367,352, entitled "3D Microscope And Methods Of Measuring Patterned Substrates", filed Jul. 23, 2010, and incorporated by reference herein. This application is also related to U.S. Pat. No. 7,729,049, entitled "3D Optical Microscope", which issued Jun. 1, 2010, U.S. Pat. No. 7,944,609, entitled "3D Optical Microscope", which issued on May 17, 2011, U.S. Pat. No. 8,174,762 entitled "3D Optical Microscope" which issued May 8, 2012, and U.S. Pat. No. 8,184,364, entitled "Illuminator For A 3D Optical Microscope", which issued May 22, 2012, all of which are incorporated by reference herein.

BACKGROUND OF THE INVENTION

Field of the Invention

The present invention relates to an optical microscope and in particular to a three-dimensional (3D) microscope and methods of measuring a patterned substrate (PS) in 3D.

Description of the Related Art

High Brightness Light Emitting Diode (HBLED) has generated tremendous interest among research communities and various industries due to its reliability, long lifetime, and environmental benefits when compared to conventional light sources. Typically, conventional HBLEDs are manufactured on transparent substrates such as sapphire, silicon carbide, and other materials. To improve light extraction efficiency, manufacturers often roughen the substrate surface to form patterns so that a greater portion of light generated in the active layer can be emitted.

U.S. Pat. No. 6,657,236, entitled "Enhanced Light Extraction In LEDs Through The Use Of Internal And External Optical Element", which issued to Thibeault on Dec. 2, 2003, and U.S. Pat. No. 7,384,809, entitled "Method Of Forming Three-Dimensional Features On Light Emitting Diodes For Improved Light Extraction", which issued to Donofrio on Jun. 10, 2008, disclose methods of creating various repeating patterns on a silicon carbide substrate to enhance the light extraction efficiency of a HBLED. As described in U.S. Pat. No. 7,384,809, images from a secondary electron microscope (SEM) can be used to verify the shapes of these patterned substrates.

U.S. Pat. No. 7,683,386, entitled "Semiconductor Light Emitting Device With Protrusions To Improve External Efficiency And Crystal Growth", which issued to Tanaka on Mar. 23, 2010, U.S. Pat. No. 7,745,245, entitled "Semiconductor Light Emitting Device", which issued to Niki on Jun. 29, 2010, and U.S. Published Application 2008/0067916, entitled "Light Emitting Device Having A Patterned Substrate And The Method Thereof", which was filed by Hsu on Jul. 30, 2007, teach various ways to generate repeating patterns on a sapphire substrate. In these references, SEM images are provided to confirm the quality of the patterned sapphire substrates.

U.S. Pat. No. 7,704,763, entitled "Highly Efficient Group-III Nitride Based Light Emitting Diodes Via Fabrication Of Features On An N-Face Surface", which issued to Fuji on Apr. 27, 2010, discloses a method of manufacturing a HBLED on a sapphire substrate, then using laser lift-off to de-bond the substrate from the diode structure. At this point, an etch process can be used to create random pyramids on an N-face GaP surface to achieve a roughened surface. Again, images from a SEM can be used in monitoring formation of the random pyramid features.

As part of the manufacturing process development and process control, manufacturers need to measure the geometry of the pattern on the substrates. These measurements typically include the shape, height, size, pitch, and space of the pattern features. Although a conventional SEM can image various patterned features, it cannot measure height information. As a result, cross-sectional SEM (x-SEM) has become the standard metrology tool in the HBLED industry. However, x-SEM is a destructive method, which requires breaking of a HBLED prior to taking a measurement. In addition, x-SEM measurement has to be carried out in a vacuum environment and therefore is slow in throughput. Furthermore, an x-SEM system is expensive to buy and maintain.

Non-destructive, non-contact optical systems have been used in the semiconductor industry for years in measuring masks on transparent substrates. For example, U.S. Pat. No. 6,323,953, entitled "Method And Device For Measuring Features On A Transparent Substrate", which issued to Blaesing-Bangert on Nov. 27, 2001, and U.S. Pat. No. 6,539,331, entitled "Microscopic Feature Dimension Measurement System", which issued to Fiekowsky on Mar. 25, 2003, teach methods for accurately measuring a line width on a photomask using an optical microscope setup. However, these methods can only measure line width, i.e. lateral dimensions, and cannot provide accurate height information.

Therefore, a need arises for a non-destructive method that is accurate, easy to use, and relatively inexpensive to measure and monitor patterned substrates. The need is met with the present invention which will be explained in the following detailed description.

SUMMARY OF THE INVENTION

A three-dimensional (3D) microscope for patterned substrate measurement can include an objective lens, a reflected illuminator, and a transmitted illuminator. The reflected illuminator can be configured to provide reflected light for a patterned substrate sample and to project an image of a patterned article onto and remove the image of the patterned article from a focal plane of the objective lens. The transmitted illuminator can be configured to provide transmitted illumination for the patterned substrate sample.

The 3D microscope can also include a focusing adjustment device, an optical sensor, and a processor. The focusing adjustment device can automatically adjust the objective lens focus at a plurality of Z steps. The optical sensor can be capable of acquiring images at each of these Z steps. The processor can control the reflected illuminator, the transmitted illuminator, the focusing adjustment device, and the optical sensor. The processor can be configured to capture first and second images at multiple Z steps, the first image with the pattern using the reflected illuminator and the second image without the pattern using one of the reflected illuminator and the transmitted illuminator.

In one embodiment, the patterned article is a piece of glass with a pre-determined pattern thereon. The optical sensor can include a charge-coupled device (CCD) camera or a complementary metal-oxide semiconductor (CMOS) camera. The transmitted illuminator can be a light emitting diode (LED) and one of a lens and a lens group. The focusing adjustment device can be a motorized mechanical Z stage or a piezo Z stage. The motorized Z stage can include a lead screw or a ball screw coupled to a linear bearing. The piezo Z stage can be mounted on a sample chuck or a microscope turret.

A method of designing a 3D microscope for measurement of a patterned substrate is also described. This method includes providing the above-described components.

A method of measuring a patterned substrate sample is also described. A patterned substrate sample is defined as including a plurality of patterned substrate features. In this method, a relative distance between the patterned substrate sample and an objective lens can be varied at predetermined steps. At one or more of the predetermined steps, the following additional steps can be performed.

An image of a patterned article can be projected onto a focal plane of the objective lens. A first image with a pattern associated with the patterned article and the sample can be captured and then stored in a first image array. The image of the patterned article can then be removed from the focal plane of the objective lens. A second image of the sample without the pattern associated with the patterned article can be captured and then stored in a second image array.

A first mask can be generated to roughly distinguish the patterned substrate features from a background area of the patterned substrate sample. This first mask is based on the second image array. A second mask can be generated to accurately distinguish the patterned substrate features from the background area. This second mask is based on the first image array and the first mask.

A top of each patterned substrate feature can be determined using the second mask and one of the first image array and the second image array. Geometric parameters of patterned substrate features can be calculated using the second mask and the top of each patterned substrate feature.

Capturing the second image can include using a reflected illuminator or a transmitted illuminator. The transmitted illuminator can be a light emitting diode (LED) and one of a lens and a lens group. Generating the first mask can include using one of color, intensity, or a combination of both color and intensity. Generating the second mask can include using a thresholding method. The geometric parameters can include size, pitch, height, space, and top size of the patterned substrate features. Varying the relative distance between the patterned substrate sample and the objective lens can include using a motorized mechanical Z stage or a piezo Z stage. The motorized Z stage can include a lead screw or a ball screw coupled to a linear bearing. The piezo Z stage can be mounted on a sample chuck or a microscope turret.

In one embodiment, the method of measuring a patterned substrate sample can include automatically varying the relative distance between the patterned substrate sample and the objective lens. This automatically varying can include a first auto-focus technique and a second auto-focus technique. The first auto-focus technique can include a conditional early exit. This conditional early exit can include determining whether more than a threshold scan range is done. When more than the threshold scan range is done, then a standard deviation can be calculated from accumulated contrast values, otherwise scanning can continue. The conditional early exit can further include determining whether the maximum contrast value is more than a specified minimum early exit threshold and a current step contrast is less than a maximum contrast by at least the standard deviation. If so, then an early exit is approved, otherwise not. The first auto-focus technique can also include capturing images while the Z stage is moving between scan steps, thereby allowing a speed of the first auto-focus to be as fast as a camera frame rate.

In one embodiment, the second auto-focus technique can have a step size smaller than that of the first auto-focus technique. The second auto-focus technique can include detecting a falling contrast pattern. This falling contrast pattern can be a scan step with peak contrast, followed at least a plurality of scan steps of lower contrast values. In one embodiment, the plurality of scan steps is four scan steps.

DETAILED DESCRIPTION OF THE DRAWINGS

The term "patterned substrate" as used herein describes a roughened surface. This roughened surface can be formed on any transparent substrate used in the HBLED industry, e.g. sapphire, silicon carbide, GaP, etc. Embodiments of patterned substrates can use repeating features or random features.

Figure 1:
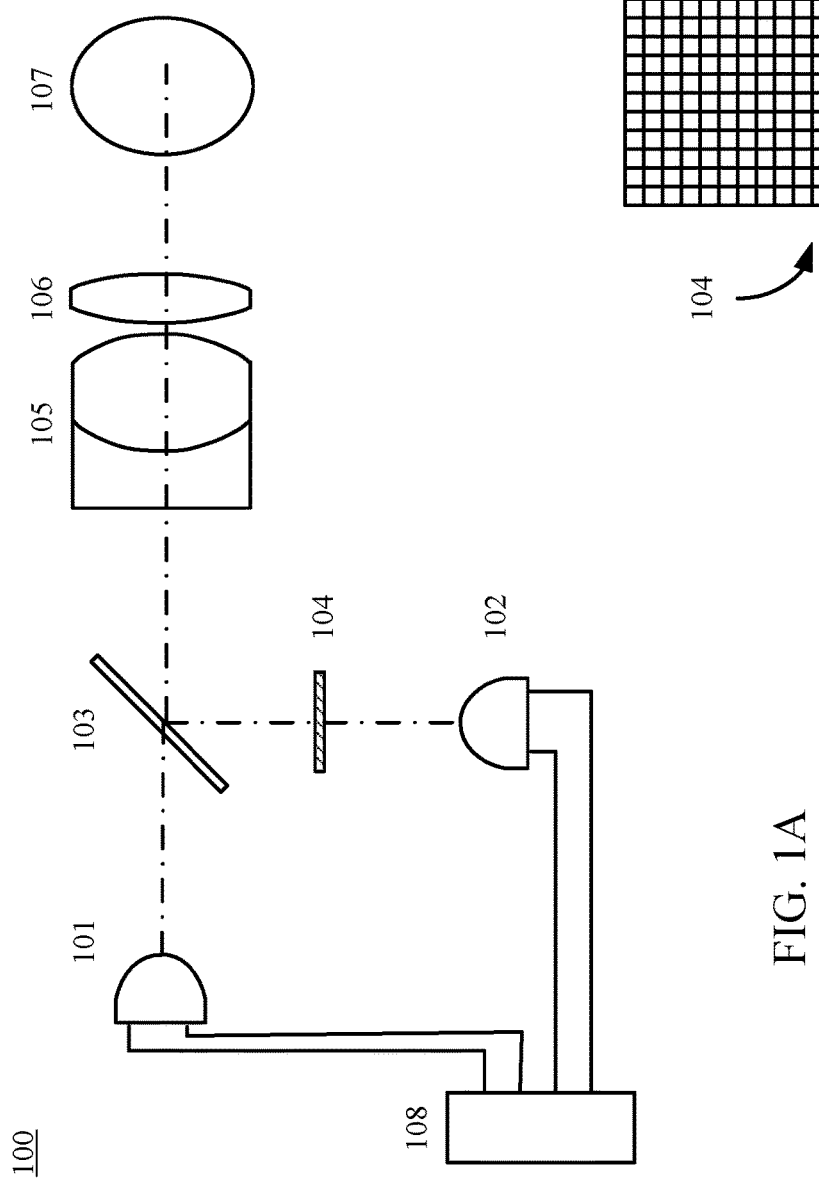
FIG. 1A illustrates an exemplary illuminator that can facilitate measuring a patterned substrate.
FIG. 1B illustrates an exemplary patterned article.

FIG. 1A illustrates an exemplary illuminator 100 configured for use in a 3D microscope for measuring patterned substrates. Illuminator 100 includes two light sources 101 and 102 that can form two light paths (shown as dash-dot lines). Specifically, a first light path includes light source 101, a first beam-splitter 103, an achromat doublet lens 105, a double convex lens 106, and a second beam-splitter 107. A second light path includes light source 102, a patterned article 104, first beam-splitter 103, achromat doublet lens 105, double convex lens 106, and second beam-splitter 107. A multi-pin connector 108 can activate light sources 101 and 102 via electrical wires.

In one embodiment, the optical components of illuminator 100 can be mounted inside a dark enclosure with two openings (not shown), e.g. a top opening and a bottom opening. The top opening can be directly above beam-splitter 107 while the bottom opening can be directly below beam-splitter 107. These two openings allow light from both light paths to interact with the outside world.

As described in further detail below, after hitting beam splitter 107, the light from one of the first and second sources travels through an objective lens and then hits the sample surface. Reflected light travels back through the objective lens, beam splitter 107, and a coupling lens (not shown). A camera receives this reflected light and forms an image (see, e.g. FIG. 2).

In a preferred embodiment, light sources 101 and 102 can include light emitting diodes (LEDs); however, other light sources such as halogen lamps, fiber-coupled lights, lasers, etc can also be used and are within the scope of this invention. Note that although lenses 105 and 106 are described as being an achromat doublet lens and a double-convex lens, those skilled in the art will understand that other types of lenses can also be used and are within the scope of this invention.

FIG. 1B illustrates one embodiment of patterned article 104. In this embodiment, patterned article 104 has a surface with a two dimensional grid pattern thereon. In other embodiments, different types of patterns, such as an array of evenly spaced opaque dots, can also be used. Indeed, any pattern will work as long as it satisfies the following conditions: (1) it has high contrast, (2) it is either regular or random, (3) it is semi-transparent, and (4) its minimum feature size matches sampling resolution of an imaging optical sensor used.

Note that patterned article 104 can be piece of glass, photographic film, or other transparent material that is capable of carrying the pattern. The patterned surface of patterned article 104 is located at the effective focal plane of the lens group including lenses 105 and 106. As described in further detail below, patterned article 104 can be used in illuminator 100 to project an image of the pattern onto the focal plane of an objective lens to create enough contrast so that 3D height information of a sample (e.g. the patterned substrate) can be obtained.

Figure 2:
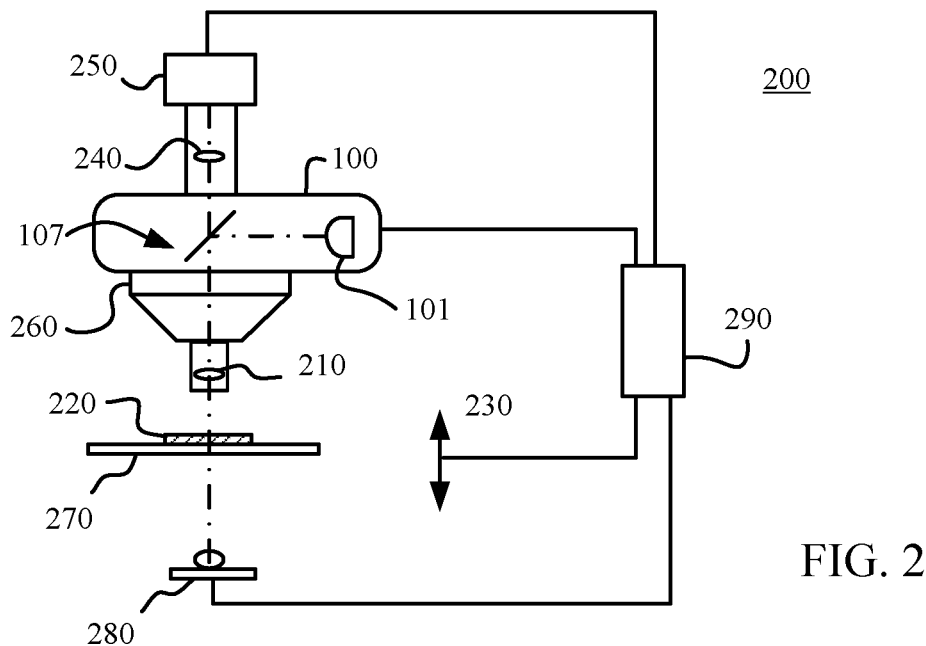
FIG. 2 illustrates a first embodiment of a 3D microscope system configured to measure patterned substrates.

FIG. 2 illustrates a first embodiment of a 3D microscope system 200 configured to measure patterned substrates. Note that illuminator 100 is shown in side view in FIG. 2. To avoid unnecessary clutter inside illuminator 100 for illustrating system 200, only light source 101 and beam splitter 107 are shown. Whenever other components of illuminator 100 are mentioned, the reader is advised to reference FIG. 1. Because illuminator 100 provides reflected illumination in this configuration, it is called a reflected illuminator. The dash-dot line in FIG. 2 illustrates the optical axis along which light travels.

A microscope objective lens 210 is mounted on a turret 260. Turret 260 can hold at least one objective lens and is mounted directly below a bottom opening of illuminator 100. When light source 101 or 102 is turned on, the lens group including lenses 105 and 106 projects an image of the light source onto the entrance pupil of microscope objective lens 210, thereby ensuring uniform illumination of a sample 220. Moreover, when light source 102 is turned on, the lens group including lenses 105 and 106 project an image of the pattern on patterned article 104 onto the focal plane of objective lens 210.

Positioning means 230 (shown as a double-headed arrow for simplicity) is provided to change the relative position between sample 220 and objective lens 210. As a result, different features on sample 220 can be brought into focus of objective lens 210. In a preferred embodiment, positioning means 230 can include a motorized Z stage or piezo Z stage. In other embodiments, other ways to vary the relative position between sample 220 and objective lens 210 can be used. For example, objective lens 210 could be mounted on a piezoelectric actuator, thereby allowing sample 220 to remain stationary while objective lens 210 moves up and down. Positioning means 230 can also include a manual or motorized XY stage (not shown), thereby allowing sample 220 to be moved in a horizontal plane. Therefore, positioning means 230 can provide an XYZ range of motion. Those skilled in the art will recognize variations of the described positioning means 230.

Coupler 240 in conjunction with objective lens 210 yields an image of sample 220 on an optical sensor 250. In a preferred embodiment, optical sensor 250 can be either a charge-coupled device (CCD) or a complementary metal-oxide-semiconductor (CMOS) camera. Coupler 240 could be of a single magnification or of a variable magnification depending on patterned substrate sample types. For example, coupler 240 could contain a 1× lens and a 2× lens mounted on a linear slider.

Light source 280 provides transmitted illumination for sample 220. As such, light source 280 is called a transmitted illuminator. In a preferred embodiment, light source 280 is an LED. In other embodiments, light sources such as halogen lamps, fiber coupled lights, lasers, and etc can be used. Sample 220 can sit on a chuck 270, which is formed from either a transparent glass plate or a metal plate with a through hole in the middle to allow light from light source 280 to go through. A processor 290 can be used to control positioning means 230, illuminator 100, light source 280, and an optical sensor 250. Processor 290 can also analyze data and create a 3D image of sample 220. In one embodiment, processor 290 can include a personal computer.

Figure 3:
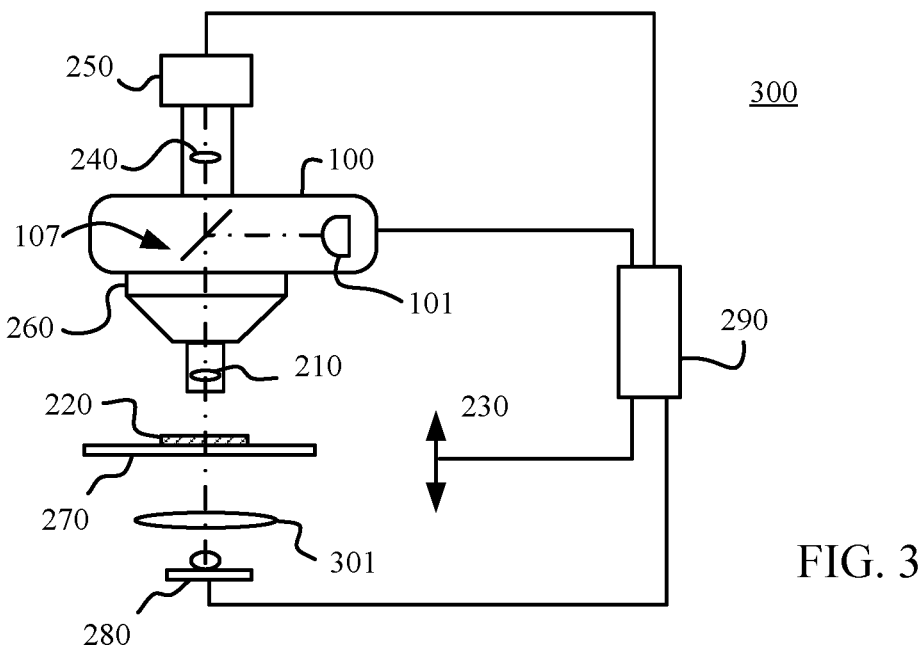
FIG. 3 illustrates a second embodiment of a 3D microscope system configured to measure patterned substrates.

FIG. 3 illustrates a second embodiment of a 3D microscope system 300 configured to measure patterned substrates. Note that components having the same reference numbers (e.g. across various drawings, such as FIGS. 2 and 3) indicate that those components provide the same functionality and therefore are not described in detail again herein. In system 300, a lens 301 can be inserted between light source 280 and chuck 270 to better concentrate transmitted light. Note that lens 301 can be a single lens or a group of lenses.

Figure 4:
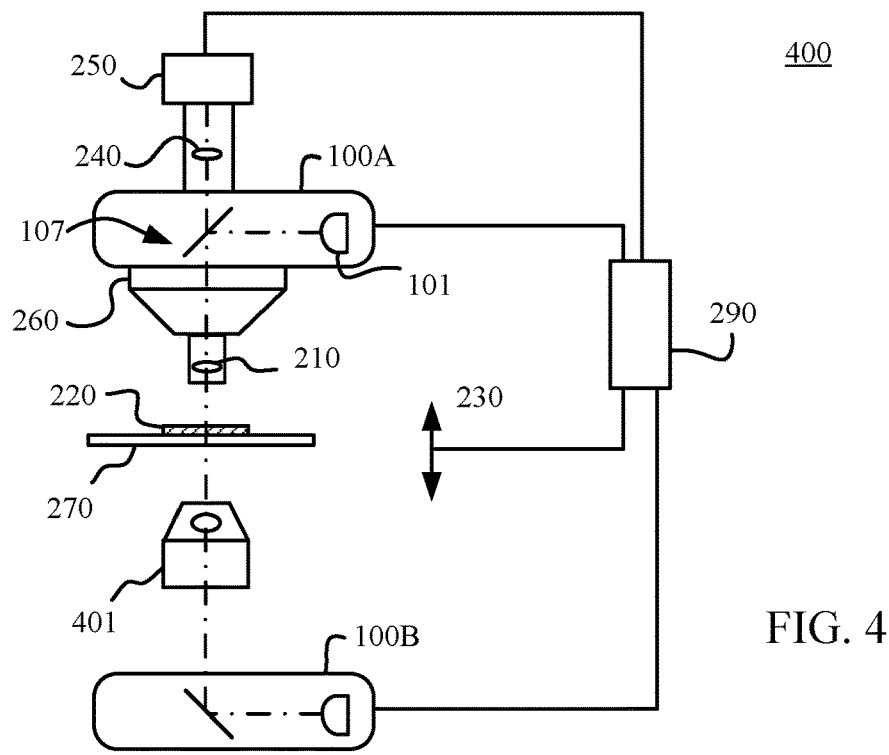
FIG. 4 illustrates a third embodiment of a 3D microscope system configured to measure patterned substrates.

FIG. 4 illustrates a third embodiment of a 3D microscope system 400 configured to measure patterned substrates. In this embodiment, two illuminators 100A and 100B (see, e.g. FIG. 1) can be included in system 400 to provide transmitted illumination as well as a means to project an image of patterned article 104 (FIG. 1) onto the focal plane of objective lens 210 from the bottom side. A condenser lens 401 can be inserted between light source 101 (in illuminator 100B) and chuck 270 to match the numeric aperture of objective lens 210 with that of the transmitted light.

Figure 5:
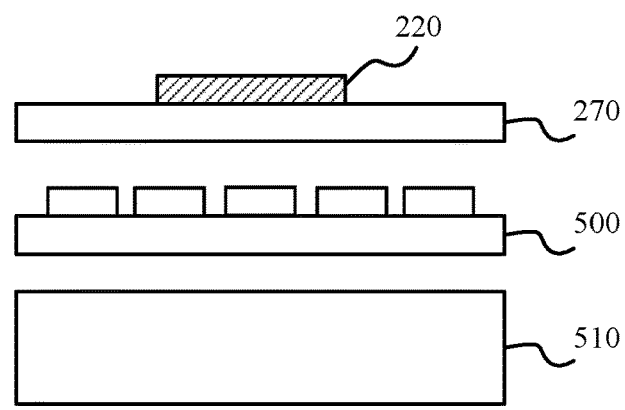
FIG. 5 illustrates an exemplary light source that can replace the light sources shown in FIGS. 2 and 3.

FIG. 5 illustrates a light source 500 that provides an alternative to light source 280 used in systems 200 and 300 (FIGS. 2 and 3). In one embodiment, light source 500 includes an array of light-emitting diodes (LEDs) that can be controlled via an electronics board. The LED array can be placed on top of a piezo stage 510. Chuck 270, with either a transparent glass plate or a metal plate with a through hole in the middle, can be placed on top of light source 500, and sample 220 can then be placed on top of chuck 270. Note that chuck 270, light source 500, and piezo stage 510 are shown spaced apart in FIG. 5 for reader comprehension and in an actual implementation would be secured together in a layered configuration.

When the region on sample 220 to be measured is moved under objective 210, certain LEDs of the array in proximity to the measured region can be turned on to provide the transmitted illumination. Piezo stage 510 allows for precise vertical movement of sample 220. Note that piezo stage 510 provides one possible embodiment of positioning means 230 (FIGS. 2 and 4). Further note that sample 220 can be placed on chuck 270 with or without light source 500. Positioning means 230 can be used to move the optics to a nominal focus relative to sample 220. Piezo stage 510 can then move sample 220 relative to the optics in higher precision steps.

Figure 6:
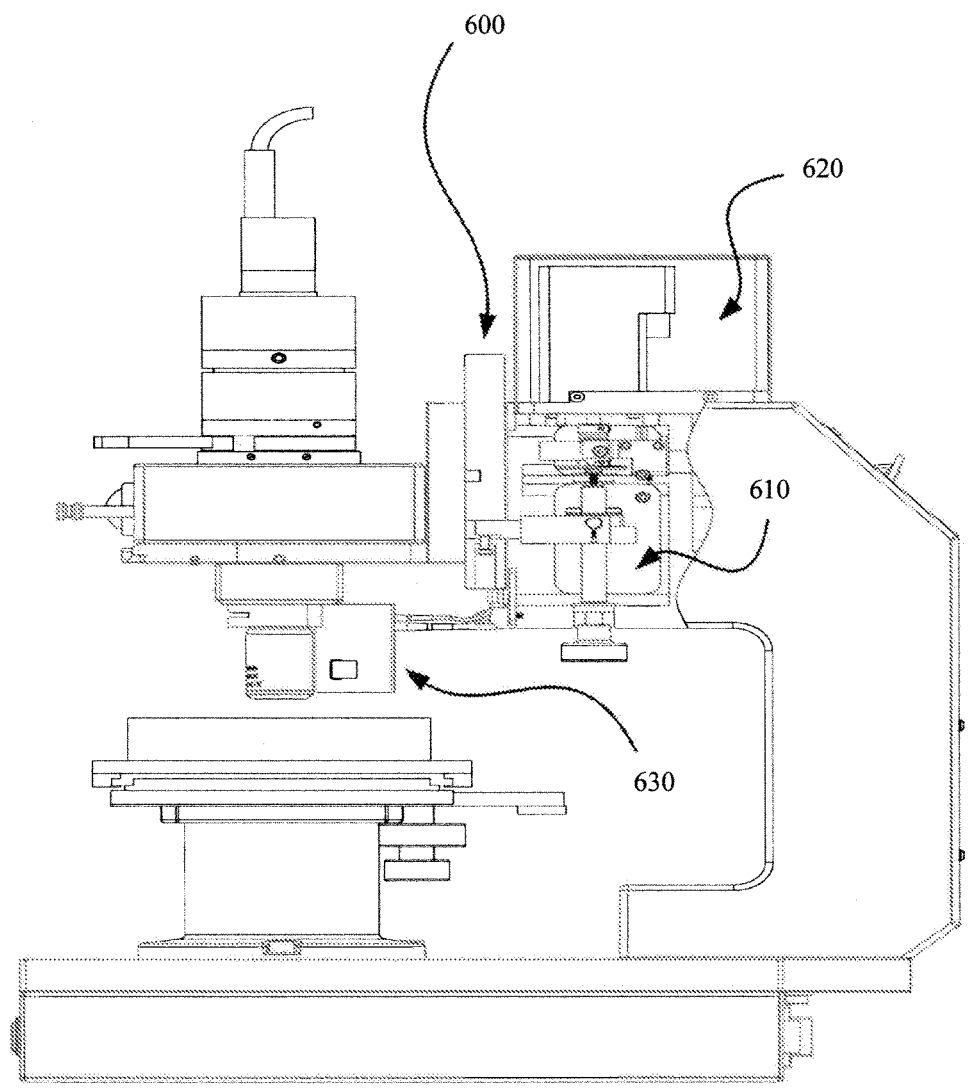
FIG. 6 illustrates exemplary positioning components that move the optics relative to the sample.

FIG. 6 illustrates another embodiment of positioning means 230 (FIGS. 2, 3, 4). In this embodiment, the positioning means can move the optics relative to the sample. This movement can be guided by a pair of linear bearings 600. A lead screw or ball screw 610 can be driven by a motor 620. To achieve high Z movement resolution, an objective lens can be mounted on a piezo Z drive 630, which in turn can be mounted on an objective turret. Piezo Z drive 630 can move the objective lens up and down in accurate steps. Note that the same type of mechanisms can also be used to move the sample relative to the optics.

In another embodiment providing high Z movement resolution, a piezo Z drive can be mounted onto lead screw/ball screw 610. In this configuration, the illuminator, the objective turret, and the objective lenses can then be moved to a nominal focus position by lead screw/ball screw 610.

A 3D microscope system can employ two methods of camera control for data and image acquisition. In a first method, for every scan the system turns on one of the first and second light sources, moves the Z stage to the desired position, and issues a trigger signal to the camera to acquire the image. Once image data is transferred from the camera to the computer memory, the system switches to the other light source (if needed) and issues another trigger signal to the camera. The system then moves the Z stage to the next position and repeats the process until the number of Z steps is completed.

In a second method, for every scan, the system moves the sample from a starting position to an ending position in a continuous motion without stopping. The camera trigger signals are generated from either the position of the encoder counts of the motor used in the lead screw/ball screw mechanism, or from the position sensor of the Z-drive or Z-stage. The system electronics then send out the trigger signals at equal distant intervals to the camera to capture the image. The interval between each trigger is programmed to match with the transfer rate of the camera. The system continuously transfers the data to the PC memory until the stage completes its motion. Note that in the second method, the system turns on one of the first and second light sources at the start of a scan and does not switch light sources during the scan. If a second pass is required, then the system runs another continuous motion scan using the other light source.

Figure 7:
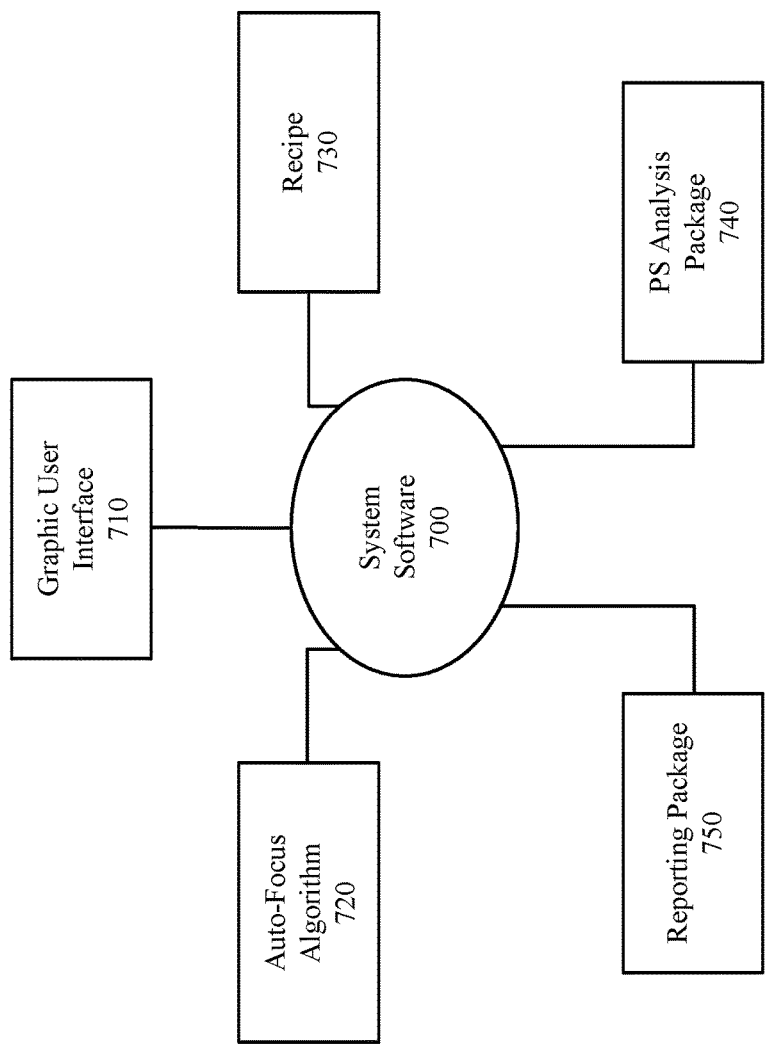
FIG. 7 illustrates exemplary software code and interface usable in the above-described 3D microscope systems.

FIG. 7 illustrates exemplary components of 3D microscope system software and interface 700 for measuring patterned substrates. An operator can interact with the 3D microscope system via graphic user interface 710. An auto-focus algorithm 720 can optimize data collection setup and enhance measurement repeatability. A recipe 730 can control data acquisition parameters and call upon the appropriate analysis algorithm. Patterned substrate analysis package 740 can include various algorithms to treat the raw data and calculate geometric parameters of a variety of patterned substrate features. Reporting package 750 can provide formatted output for patterned substrate feature size, pitch, height, space, etc.

Due to sample thickness variations, different locations on the patterned substrate sample may have different Z positions relative to the objective lens. In addition, a patterned substrate sample is not flat but has surface texture, i.e. a vertical profile. Therefore, before each patterned substrate measurement, the point to be measured on the sample needs to be focused. This focusing can be done manually, but the precision or repeatability of the resulting start point can vary. To minimize this variation of the start point for a repeatable patterned substrate measurement, an auto-focus procedure can be used to start scanning from a consistent starting Z position.

Note that a simple, conventional method to search for the best focus would be to command the Z stage to step through the whole search range at a predefined step size, and at each step, wait until the Z motion settles, command the camera to capture an image, and then wait for the image data to arrive. After the image contrast from all steps is analyzed, the Z position corresponding to the highest contrast could be determined. The position of highest contrast would be the best guess focus Z position. While this simple method works and is accurate, it is undesirably slow.

An auto-focus technique in accordance with the present invention can take advantage of the 3D microscope image contrast from the projected pattern as well as from the sample itself. When part of the sample surface is brought close to the focal plane, the corresponding part of the image contrast gets higher and will reach a peak when that part of the sample surface is at the focal plane. The auto-focus technique described herein has two-passes: the first pass being optimized for speed and the second pass being optimized for accuracy.

Figure 8:
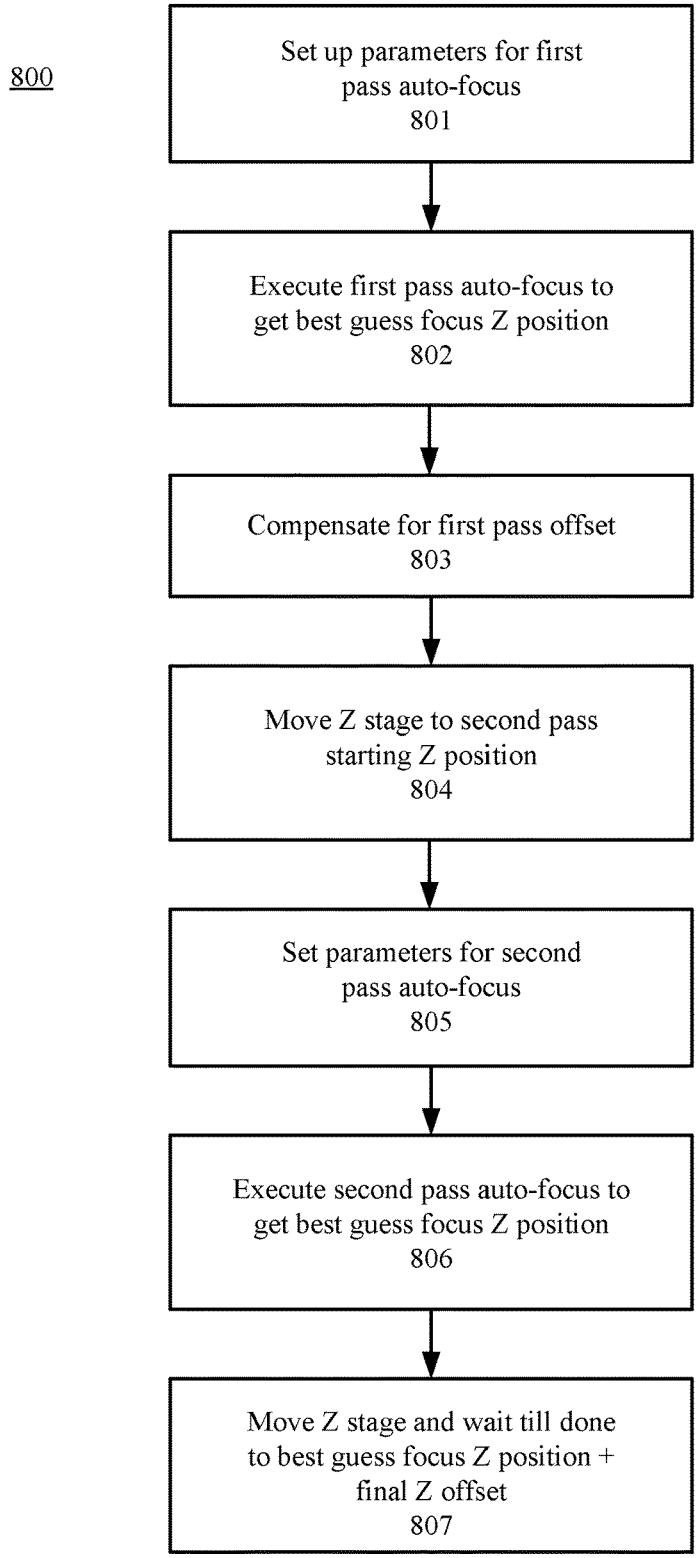
FIG. 8 illustrates an exemplary two-pass autofocus technique.

FIG. 8 illustrates an exemplary two-pass auto-focus technique 800. In technique 800, the positioning means is assumed to be a Z stage, which can move the patterned substrate sample up and down. In step 801, the system can set up the parameters for the first pass. Exemplary parameters can include a scan range, a step size and speed, and an early exit threshold (described in detail below). In one embodiment, the early exit threshold can be user-provided. In step 802, the first pass of the auto-focus is executed, which yields a best guess focus Z position. In step 803, the offset to the first pass best guess is determined based on empirical results (e.g. previous experiments with typical systems). Table 1 (below) shows typical offsets for various step sizes and camera frame rates:

TABLE 1

| Frame rate (fps) | Step size (microns) | Offset (microns) |
| --- | --- | --- |
| 1 to 15 | up to 0.5 | 0 |
| 1 to 15 | more than 0.5 | 1 |
| 16 to 60 | up to 0.5 | 1 |
| 16 to 60 | more than 0.5 | 2 |
| faster than 60 | up to 0.5 | 3 |
| faster than 60 | more than 0.5 | 5 |

Figure 9A:
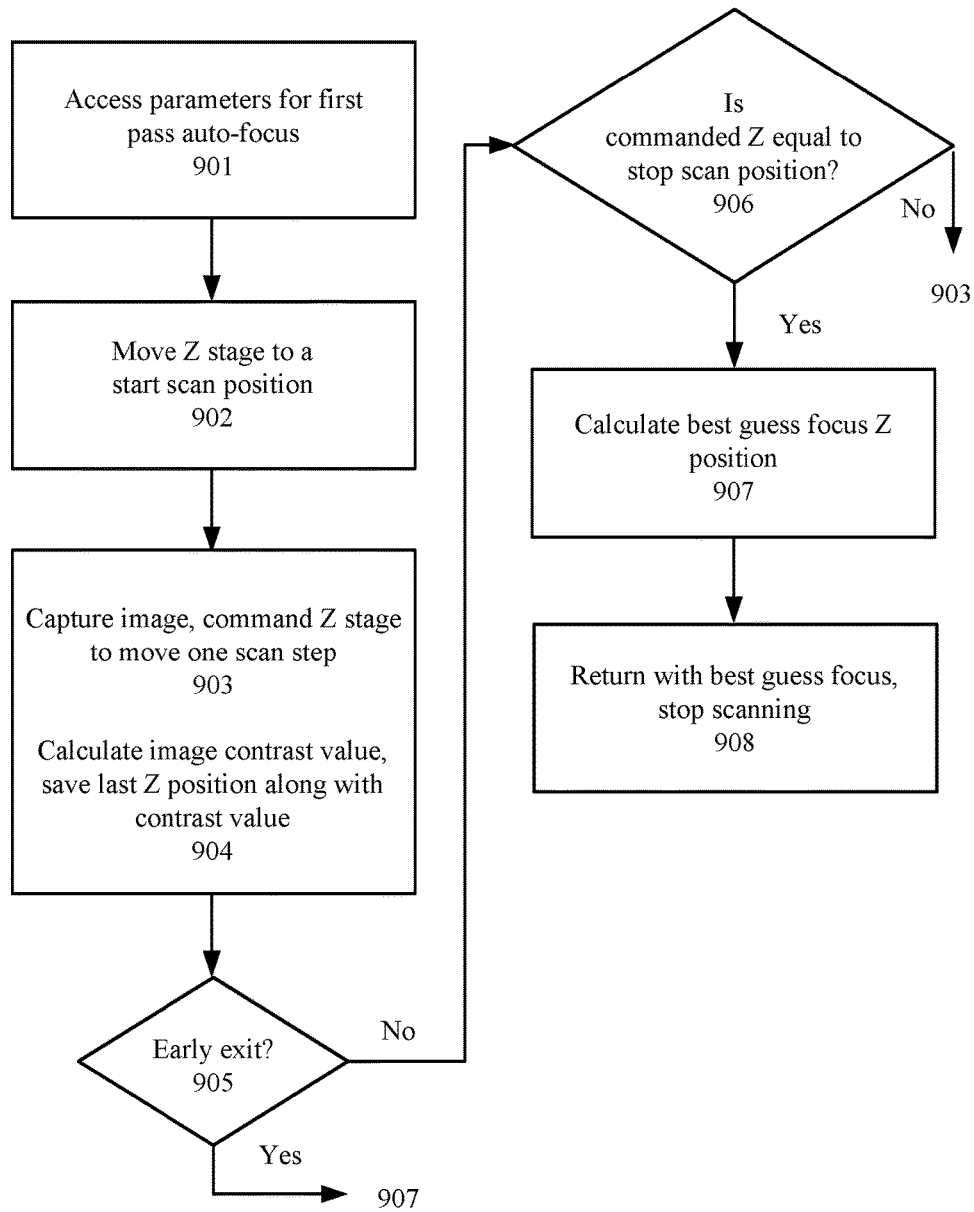
FIG. 9A illustrates an exemplary autofocus first pass technique.

This offset can be used to generate a more accurate first pass best guess focus Z position (described in further detail in reference to FIG. 9A).

In step 804, the Z stage is moved to a second pass starting Z position. In one embodiment, the second pass starting Z position is calculated to be at half of the second pass scan range below the first pass best guess focus Z position.

In step 805, parameters for the second pass auto-focus can be set. For example, in one embodiment, the step size can be set to be half of that in the first pass to improve resolution. Moreover, the second pass scan range can be set to N times the first pass step size, wherein N is a positive integer or fraction. In one embodiment, the scan range is set by a user. In another embodiment, the scan range is set by the recipe, which is specific to a particular sample and system configuration. An optimized choice for the second pass scan range may be determined by the accuracy of the first pass best guess focus Z position. The second pass will be slow if its scan range is set too large. However, if the scan range is set too small, the actual focus may not be covered, thereby potentially missing the true best focus. In one embodiment, the second pass scan range may be larger or smaller than 8 times the first pass step size.

In step 806, the second pass auto-focus can be executed to generate a second pass best guess focus Z position. In step 807, the Z stage can be moved to a best guess focus Z position plus the final Z offset. This positioning can ensure that the patterned sample measurement can start from a consistent specific point.

FIG. 9A illustrates exemplary steps for a first pass auto-focus (usable for step 802). In step 901, the parameters for the first pass auto-focus are accessed. In step 902, the Z stage is moved to a start scan position. In step 903, an image is captured and the Z stage is commanded to move one scan step. In step 904, the image contrast value is calculated, then that contrast value and its corresponding Z position can be saved in memory.

Notably, in step 903, Z stage movement can be triggered when image frames are captured rather than arrival at designated scan steps. Thus, images can be captured while the Z stage is moving between scan steps, thereby allowing the auto-focus speed to be as fast as the camera frame rate. To speed up each scan step, the first pass auto-focus can run the camera at its fastest frame rate, which occurs in a free running, continuous capture mode where images are continuously captured and transferred to processor 290 (FIG. 2). After each image frame is captured, the processor commands the Z stage to move to the next scan step, calculates the image contrast, and then waits for the next image frame. If the next image frame arrives before the Z stage has completed its motion, the algorithm nevertheless issues a command to move to the next scan step. Note that because calculation of the contrast value is performed during movement of the Z stage, steps 903 and 904 are shown in the same stage in FIG. 9A.

Because the algorithm does not wait for the Z stage to finish its motion, the actual Z position corresponding to the image received will be less than the commanded Z position. This difference is typically small, if the camera frame rate is slow, but becomes more significant when the camera is fast. Because of this difference between commanded and actual Z position, the best guess focus Z position corresponding to the commanded Z position will probably be shifted from the actual best guess focus Z position. Therefore, a calibration offset table linking this shift with the step size and camera frame rate (see, step 803, FIG. 8) can be used to compensate for some of this shift, thereby making the first pass best guess focus Z position more accurate.

Step 905 determines whether a focus has been found (described in further detail in reference to FIG. 9B), which would allow an early exit. If an early exit is not possible, then step 906 checks whether the commanded Z position is equal to a stop scan position. If so, then step 907 calculates a first pass best guess focus Z position. The first pass best guess focus Z position can be the Z position corresponding to the best contrast from the captured images of the scan. At this point, step 908 can output a first pass best guess focus Z position and stop scanning. If an early exit is possible in step 905, then the first pass technique can proceed directly to step 907 and skip step 906. If the commanded Z position is not equal to a stop scan position, then the first pass technique can return to step 903 for further scanning.

Figure 9B:
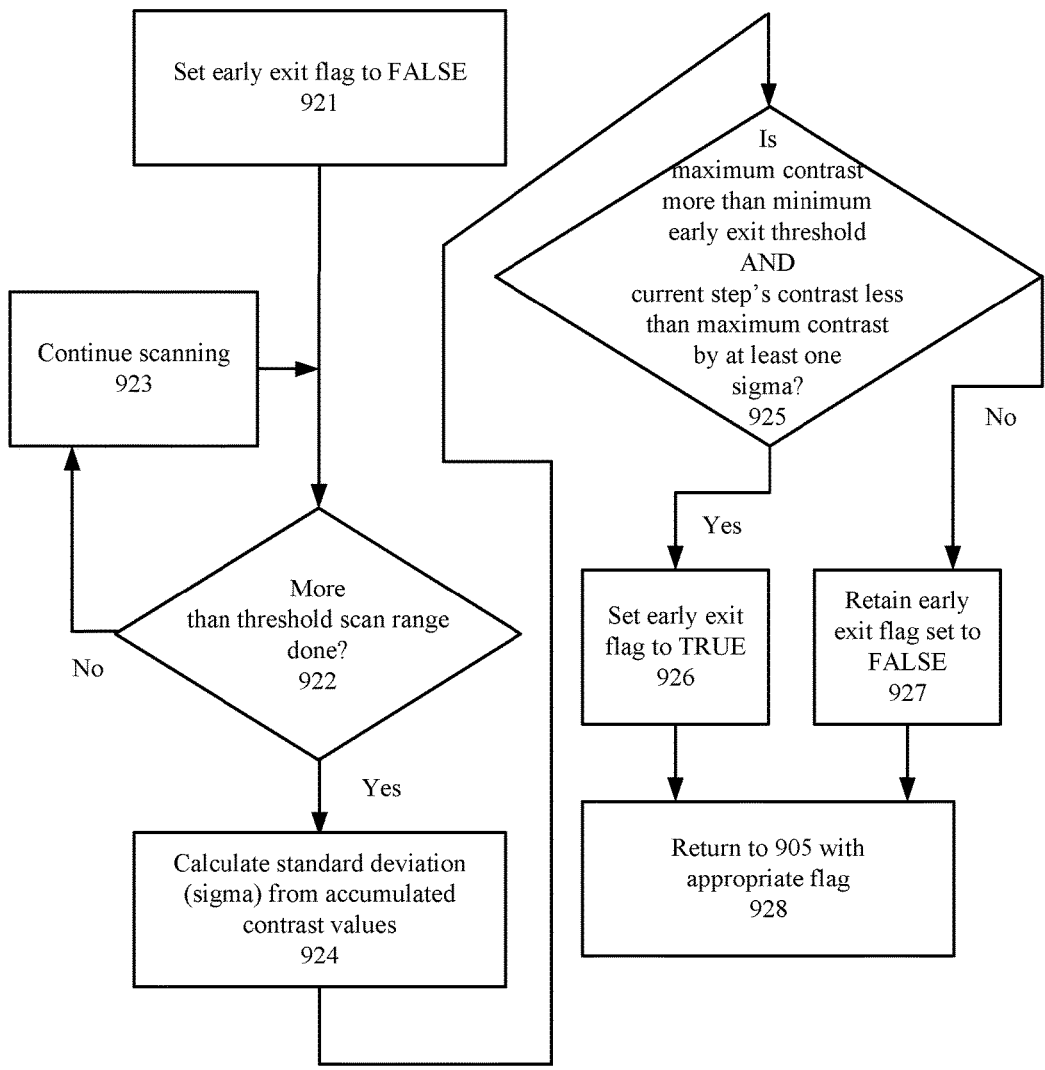
FIG. 9B illustrates an exemplary autofocus first pass early exit determination technique.

FIG. 9B illustrates an exemplary technique for a first pass early scan exit determination technique. As noted above, if a valid focus is found, then the first pass can advantageously stop early without scanning the rest of the scan range. In general, a focus can be identified if the image contrast values from the captured images show a pattern of rise and fall. In order to quantify the relative contrast rise and fall, this technique requires a minimum number of scan steps to get a meaningful statistics calculation of the image contrast. In one embodiment, a minimum of half of the total scan steps is required, but less than half or more than half is also possible.

Step 921 of this early exit technique can set a default flag of no early exit (i.e. early exit is FALSE). Step 922 can determine whether more than a threshold scan range (i.e. a minimum number of scan steps) is done. For example, in one embodiment, if less than half of the scan steps are scanned, then step 923 continues scanning and subsequently returns to step 922. If more than half of scan steps are scanned, then step 924 can calculate the standard deviation (sigma) from the accumulated contrast values.

Step 925 can determine whether the maximum contrast value is more than a specified minimum early exit threshold and the contrast value of current scan step is at least one standard deviation below that of the maximum contrast value of the accumulated contrast values. For a typical image with a contrast value between 0 and 1000, a threshold of 10 would be reliable for most samples. If so, then a focus is found and step 926 can set the early exit flag to TRUE. If not, then a focus is not found and step 927 can retain the early exit flag setting of FALSE. Step 928, which follows either step 926 and or step 927, can return to the first pass technique with an appropriate flag for step 905.

Figure 9C:
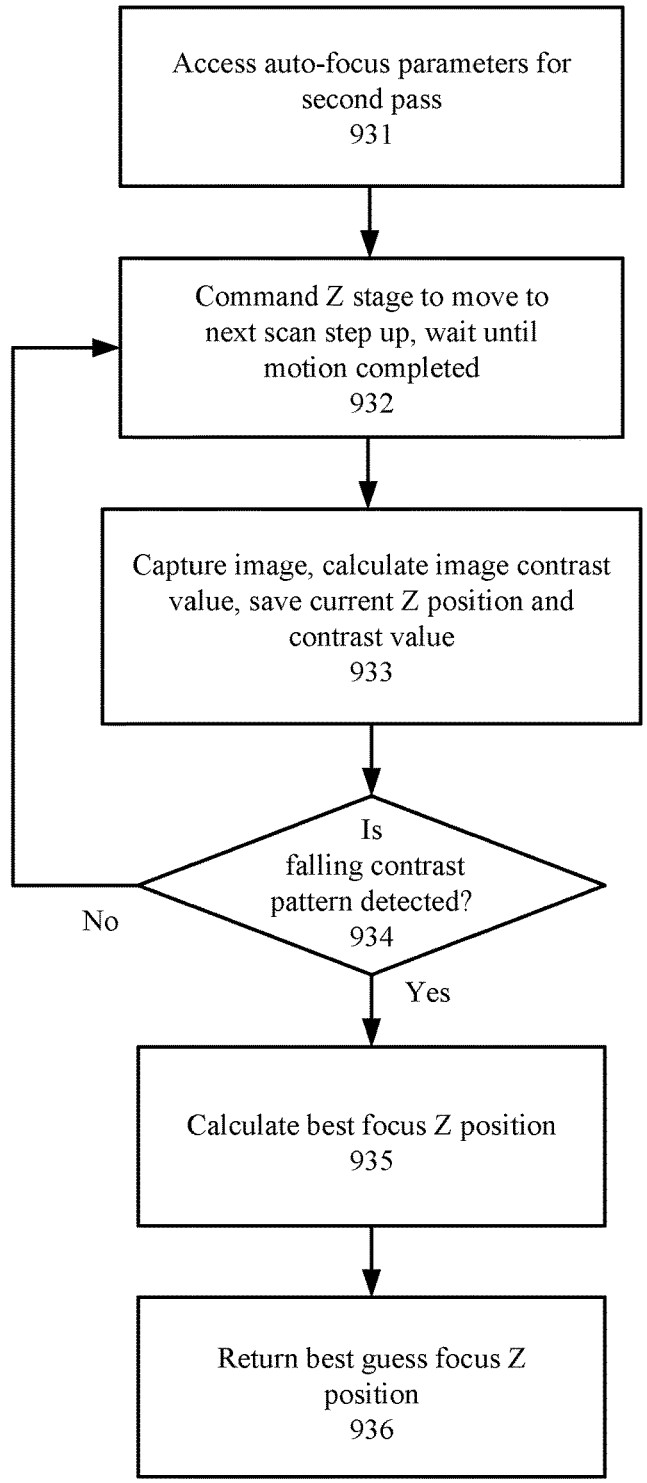
FIG. 9C illustrates an exemplary autofocus second pass technique.

FIG. 9C illustrates an exemplary auto-focus second pass technique. Step 931 can access the auto-focus parameters for the second pass and move the Z stage to its starting position. Step 932 can move the Z stage to the next scan step and wait until movement is done. Step 933 can capture an image frame at that scan step, calculate its contrast value, and save (in memory) that contrast value as well as its corresponding commanded Z position.

Because the focus position is expected to be within the second pass starting and ending positions, the saved contrast values in the second pass are expected to have a rise and fall pattern. Therefore, at step 934, a simple check of falling contrast values can be done to determine if focus is found, thereby indicating that the second pass auto-focus is done. Notably, because the second pass scan step size is smaller than that of the first pass, the rise and fall pattern may not be sharp (for example, several scan steps may have the same or similar maximum contrast value, thereby not changing contrast values significantly). Also, because the search range of the second pass only needs to cover the uncertainties of the first pass, it can be much smaller than that of the first pass. As a result, the number of search steps in the second pass steps is small. In the preferred embodiment, the maximum number of second pass search steps is 19. Statistics calculated on such limited number of contrast values may not be meaningful. Therefore, in one embodiment, a falling contrast value can be defined to be a scan step with peak contrast, followed by 4 scan steps of lower contrast values. A value of less than 4 makes the second pass stop sooner, and a value of more than 4 makes the second pass more accurate.

If a falling contrast pattern is detected, then step 935 can calculate the best guess focus Z position. In one embodiment, the best guess focus Z position can be the middle of the Z position range corresponding to the middle of the maximum contrast range.

As described above, a two-pass patterned sample measurement technique can include first and second passes. The first pass auto-focus can advantageously stop the focus search early without going through all the steps. Moreover, the images can be captured while the Z stage is moving between scan steps, thereby allowing the auto-focus speed to be as fast as the camera frame rate. To further improve upon the first pass autofocus accuracy, the second pass can search at a smaller step size within a small range around the best guess focus Z position found in the first pass.

Additional improvements on the two-pass auto-focus technique can also be provided. For example, in one embodiment, different criteria can be used for determining maximum contrast or best focus. That is, instead of calculating the overall contrast of the whole image, the contrast of a portion of the image, or the contrast of several different portions of the image can be calculated and then used to determine the maximum contrast for the best focus.

Because the goal of the auto-focus procedure is to position the patterned substrate sample at a consistent point to start the patterned sample measurement, other means, including different auto-focus methods, such as auto-focus method using image intensity with a confocal optical setup, or using focus signal from a separate focus sensor, instead of image contrast as described above, can be used in other embodiments to achieve the same results. Such variations are within the scope of this invention.

In yet another embodiment, a user can also specify the position found from the auto-focus algorithm to represent the middle, the bottom, or the top of scan range (or any position in between). This specificity is needed because the auto-focus algorithm will find the best focus consistently at the highest average contrast surface. The highest contrast surface position can be at the base, the middle, or the top of the patterned sample structure depending on its shape and composition. This extra control can be specified in the GUI/recipe, thereby tailoring the GUI/recipe for different patterned sample wafers or chips.

Figure 10:
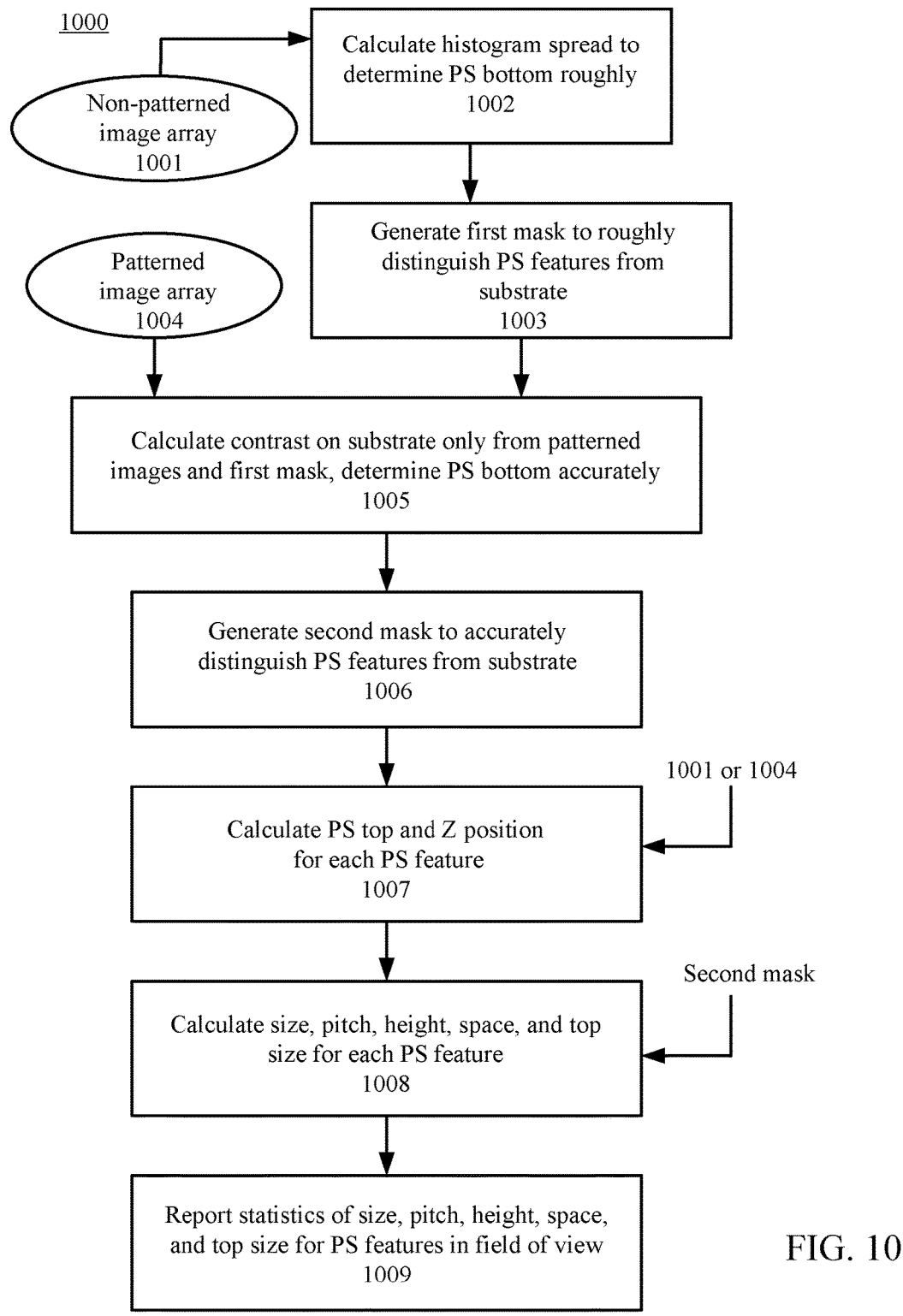
FIG. 10 illustrates an exemplary patterned substrate measurement technique.

FIG. 10 illustrates an exemplary patterned substrate measurement technique 1000. Technique 1000 can receive both patterned image array 1004 and non-patterned image array 1001, which includes images captured at multiple Z positions, as inputs. These inputs can be utilized in measuring the size, pitch, height, space, and top size of the patterned substrate features. Note that the term "non-patterned image array" refers to an array of images taken without the presence of patterned article 104 (see FIG. 1A) in the imaging path. In contrast, the term "patterned image array" refers to an array of images taken with the presence of patterned article 104 in the imaging path.

For certain patterned substrate features, e.g. such as cone and triangular features, non-patterned images are collected with the transmitted illumination (see, e.g. embodiments of FIGS. 2, 3, 4) and then stored in non-patterned image array 1001. For other patterned substrate features, such as flat top features, non-patterned images are collected with reflected illumination and then stored in non-patterned image array 1001. In one embodiment, software-implemented binary masks (described below) can be used to roughly and accurately distinguish the patterned substrate features from the substrate (also referred to as the background because the patterned substrate features are above the plane of the substrate) as well as measure the patterned substrate features. Technique 1000 is now explained in detail.

Step 1002 can calculate a histogram spread for non-patterned image array 1001 as an indication of either color or intensity distribution. Note that the spread of the histogram tends to be at the maximum when the Z position is around the bottom of the patterned substrate features, i.e. at the substrate. Therefore, the Z position of the substrate can be roughly determined by obtaining the maximum of the histogram spread. Step 1003 can generate a first mask by applying a threshold indicated by the median of the histogram to non-patterned image array 1001 at this Z position. Note that the first mask is a binary mask having an opaque background with transparent features that roughly represent the bases of the patterned substrate features. Note that this binary mask is implemented in software and is not a physical mask.

The first mask can be used to roughly distinguish the patterned substrate features from the substrate. The boundary between the patterned substrate features and the substrate may not be very accurate because of noise introduced in part from the actual shape of the patterned substrate features.

Step 1005 can use patterned image array 1004 and the first mask (from step 1003) to calculate the contrast on the substrate at this Z position. As noted above, the patterned substrate feature designations of the first mask typically have noise issues. Therefore, step 1005 can use the first mask to eliminate those areas from the contrast calculation. As a result, the contrast calculation with patterned image array 1004, but without the roughly designated patterned substrate features, allows an accurate Z position of the substrate to be determined. In one embodiment, this accurate Z position can be based on the maximum contrast value.

Figure 11:
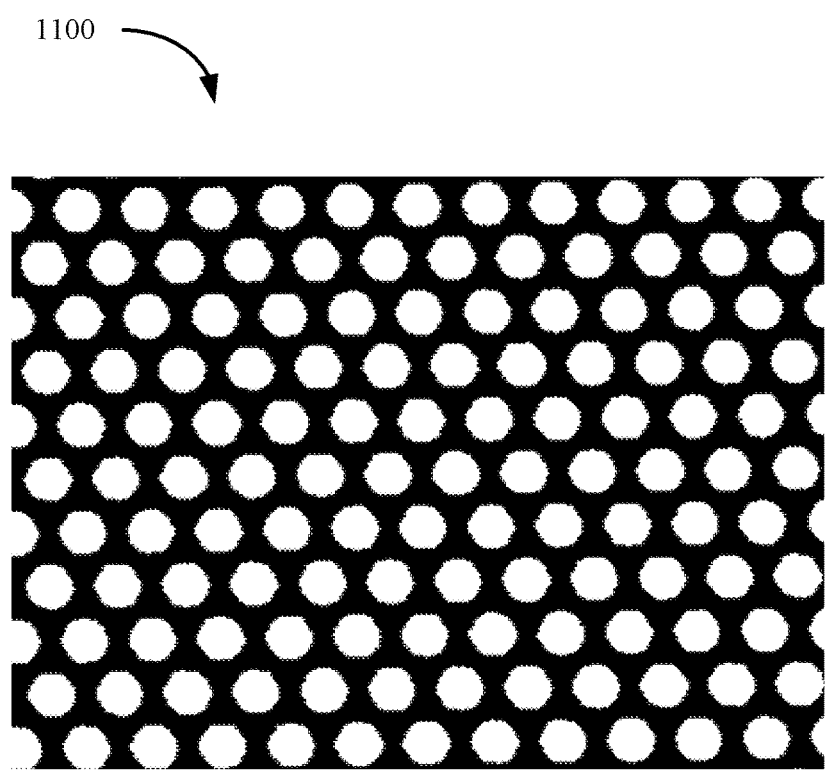
FIG. 11 illustrates an exemplary binary mask that can facilitate distinguishing patterned substrate features from a substrate.

Step 1006 can generate an accurate binary mask, called a second mask, by applying a threshold indicated by the median of the histogram to non-patterned image array 1001 at this Z position. This second mask can be used to accurately distinguish the patterned substrate features from the substrate. FIG. 11 illustrates an exemplary second mask 1100, which shows the bases of the patterned substrate features in white and the substrate in black. Note that based on the shape of the white features, the patterned substrate features are cylinders (also called flat tops), domes, or cones.

Step 1007 can use the second (i.e. accurate) mask and either the non-patterned image array 1001 or the patterned image array 1004 to calculate the top and the Z position of each of the patterned substrate features. Information from the recipe (described below in reference to FIG. 12) regarding the patterned substrate feature shape can be used in step 1007 to determine whether to use non-patterned image array 1001 or patterned image array 1004. Specifically, if the shape of the patterned substrate features is conical or triangular, then step 1007 can use non-patterned image array 1001. However, if the shape of the patterned substrate features is flat (e.g. cylindrical), then step 1007 can use patterned image array 1004. In one embodiment, interpolation can be used to take into account possible variations and/or combinations in pattern substrate feature shapes. The calculations performed in step 1007 can be based on contrast computations for pixels inside of each feature.

Step 1008 can calculate the size, pitch, height, space, and top size of each patterned substrate feature based on the top and Z position values computed in step 1007 and the second mask. Size can be defined as a diameter for a circular patterned substrate feature or a height for a patterned substrate having an equilateral triangular base. Pitch can be defined as a distance between the center of a current patterned substrate feature and the center of a neighboring patterned substrate features. In one embodiment, the average of the distances between all neighboring patterned substrate features can be calculated and used as the pitch. Height can be determined by the absolute difference of the maximum Z position and the minimum Z position within the patterned substrate feature. Space can be defined as the difference between the pitch and the size. Note that the top size only applies to a patterned substrate feature having a flat plane on its top. Statistics of these values, such as average, median, standard deviation and others can be obtained over the whole field of view to get more reliable readings of the patterned substrate features. Step 1009 can report these values.

Figure 12:
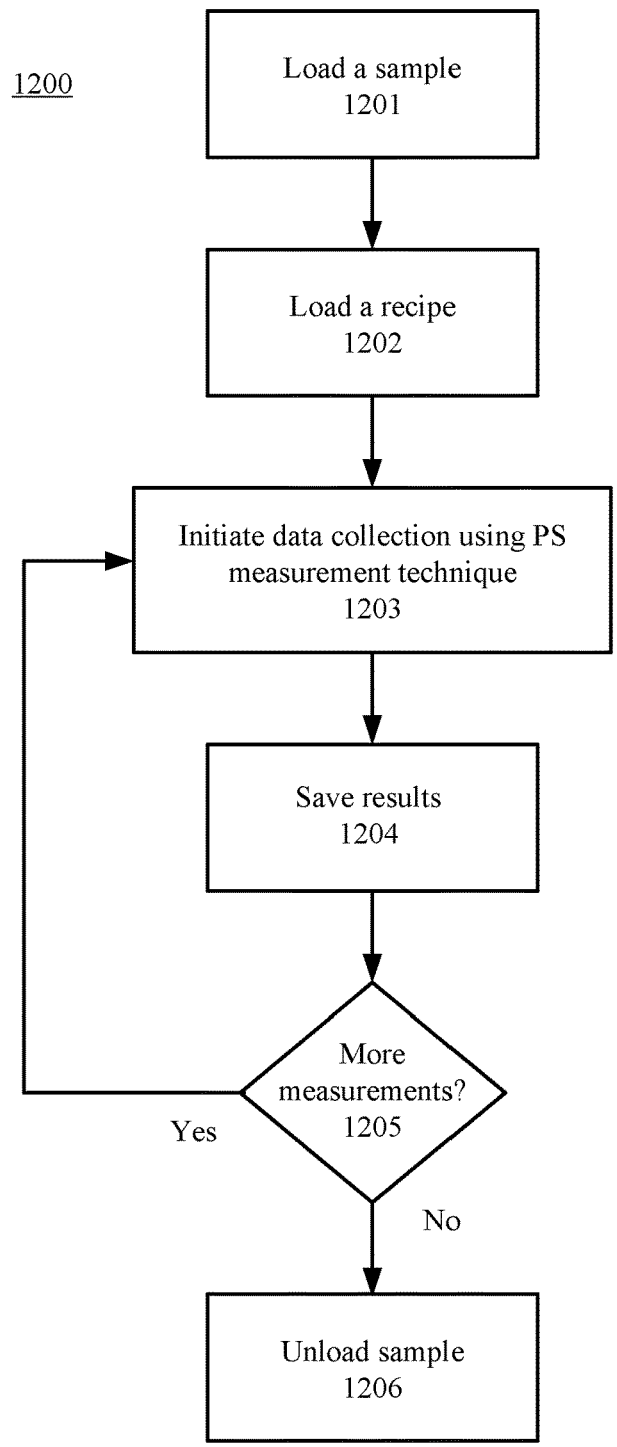
FIG. 12 illustrates an exemplary measurement technique using a manual 3D optical system.

FIG. 12 illustrates exemplary steps in a patterned substrate measurement technique 1200 using a manual 3D microscope system in accordance with one embodiment. Note that a manual system is defined as one having a manual XY stage. At step 1201, an operator can load a patterned substrate sample, choose an objective lens, and locate a measurement spot on the sample. For patterned substrate measurement, an objective lens (i.e. objective lens 210, FIG. 2) having a 100× magnification lens with 0.9 or 0.95 numerical aperture can be chosen. In step 1202, the operator can load a recipe corresponding to the sample. In step 1203, the operator can initiate data acquisition by clicking on a button. At that point, the system can get and analyze raw data to provide the necessary output information. In step 1204, the operator can save the results and/or conduct specific, selected analysis. In step 1205, the operator can decide whether more spots on the sample are to be measured. If so, then the technique can return to step 1203. If not, then technique 1200 can proceed to step 1206, at which point the operator can unload the sample and the patterned sample measurement technique ends.

Figure 13:
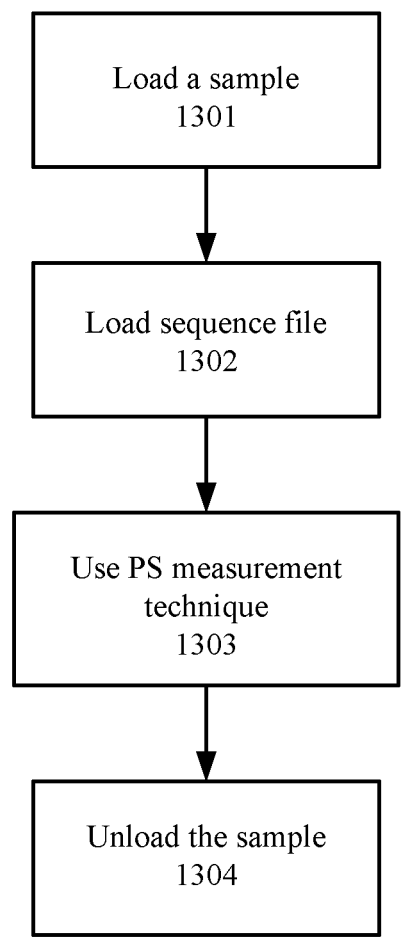
FIG. 13 illustrates an exemplary measurement technique using an automatic 3D optical system.

FIG. 13 illustrates exemplary steps in a patterned substrate measurement technique using an automated 3D microscope system in accordance with another embodiment. An automated system is defined as one with a motorized XY stage. In step 1301, an operator can load a patterned substrate sample and choose an objective lens. For patterned substrate measurement, an objective lens having a 100× magnification lens with 0.9 or 0.95 numerical aperture typically is chosen. In step 1302, the operator can load a sequence file that includes, among other things, a recipe corresponding to the sample and a map of predetermined measurement locations. In step 1303, the operator can initiate data acquisition, e.g. by clicking a button. At that point, the system will move to the first measurement spot on the sample, take raw data, analyze the raw data to provide the necessary result, and save the results into a file. When the measurement is done, the sample is automatically moved to the next spot. This process will be repeated until all the designated locations are measured and the results are saved. At step 1304, the operator can unload the sample, thereby terminating the patterned sample measurement technique.

Compared to prior art, the 3D microscope system described herein has several advantages. Specifically, the 3D microscope system is easy to use, is based on a non-contact, non-destructive method, offers a low cost of ownership among a class of existing patterned sample measurement tools, notably, provides fast, accurate, and repeatable measurement on key parameters that matter to patterned substrate manufacturers. Among these parameters are the size, pitch, height, and space of patterned substrate features.

The embodiments described herein are not intended to be exhaustive or to limit the invention to the precise forms disclosed. As such, many modifications and variations will be apparent. Accordingly, it is intended that the scope of the invention be defined by the following Claims and their equivalents.

The invention claimed is:

1. A method of measuring a patterned substrate sample, the patterned substrate sample including a plurality of patterned substrate features, the method comprising:
varying a relative distance between the patterned substrate sample and an objective lens at predetermined steps;
at one or more of the predetermined steps:
projecting an image of a patterned article onto a focal plane of the objective lens;
capturing a first image with a pattern associated with the patterned article and the patterned substrate sample, and storing the first image in a first image array; and
capturing a second image of the patterned substrate sample without the pattern associated with the patterned article, and storing the second image in a second image array;
using the second image array to roughly estimate a bottom position of the patterned substrate features;
using the roughly estimated bottom position and the second image array to identify first locations of the patterned substrate sample that do not include the plurality of patterned substrate features;
using the first image array and the first locations to accurately determine the bottom position of the patterned surface features;
using the accurately determined bottom position and the second image array to identify second locations of the patterned substrate sample that include the plurality of patterned substrate features;
determining a top of each patterned substrate feature based on the second locations and one of the first image array and the second image array; and
calculating geometric parameters of patterned substrate features using the second locations, the accurately determined bottom position, and the top of each patterned substrate feature.

2. The method of claim 1, wherein capturing the second image includes using one of a reflected illuminator and a transmitted illuminator.

3. The method of claim 2, wherein the transmitted illuminator is a light emitting diode (LED) and one of a lens and a lens group.

4. The method of claim 1, further comprising calculating a histogram spread for the second image array to roughly estimate the bottom position of the patterned substrate features.

5. The method of claim 1, wherein using the first image array and the first locations to accurately determine the bottom position of the patterned surface features includes: performing a contrast calculation using only portions of the first image array associated with the first locations.

6. The method of claim 5, wherein the accurately determined bottom position is based on a maximum contrast value of the contrast calculation.

7. The method of claim 1, wherein the second locations of the patterned substrate are determined using a threshold method.

8. The method of claim 1, wherein the geometric parameters include size, pitch, height, space, and top size of the patterned substrate features.

9. The method of claim 1, wherein varying the relative distance between the patterned substrate sample and the objective lens at predetermined steps is performed automatically using an autofocus technique.

10. The method of claim 9, wherein the auto-focus technique includes a first auto-focus technique and a second auto-focus technique.

11. The method of claim 10, wherein the first auto-focus technique includes a conditional early exit.

12. The method of claim 11, wherein the conditional early exit includes determining whether more than a threshold scan range is done.

13. The method of claim 11, wherein the first auto-focus technique includes capturing images while varying the relative distance between the patterned substrate sample and the objective lens.

14. The method of claim 11, wherein the second auto-focus technique has a step size smaller than that of the first auto-focus technique.

15. The method of claim 14, wherein the second auto-focus technique includes detecting a falling contrast pattern.

* * * * *